US008217022B2

(12) United States Patent
Osmak et al.

(10) Patent No.: US 8,217,022 B2
(45) Date of Patent: Jul. 10, 2012

(54) ANALOGUES OF 1,3-BIS(4-NITROPHENYL)TRIAZENES, THEIR PHARMACEUTICALLY ACCEPTABLE SALTS AND N-ACYL DERIVATIVES FOR TUMOUR TREATMENT

(75) Inventors: Maja Osmak, Zagreb (HR); Slovenko Polanc, Ljubljana (SI); Tamara Cimbora Zovko, Zagreb (HR); Anamaria Brozovic, Zagreb (HR); Marijan Kocevar, Ljubljana (SI); Vita Majce, Ljubljana (SI); Branko Alic, Ljubljana (SI)

(73) Assignee: Rudjer Boskovic Institute (HR)

( * ) Notice: Subject to any disclaimer, the term of this patent is extended or adjusted under 35 U.S.C. 154(b) by 2 days.

(21) Appl. No.: 13/090,978

(22) Filed: Apr. 20, 2011

(65) Prior Publication Data
US 2011/0224412 A1   Sep. 15, 2011

Related U.S. Application Data

(63) Continuation of application No. PCT/HR2010/000006, filed on Mar. 9, 2010.

(30) Foreign Application Priority Data

Mar. 11, 2009   (HR) .............................. P 20090144 A

(51) Int. Cl.
C07C 245/24   (2006.01)
A61K 31/655   (2006.01)
(52) U.S. Cl. ......................... 514/151; 534/553; 534/554
(58) Field of Classification Search ........................ None
See application file for complete search history.

(56) References Cited

U.S. PATENT DOCUMENTS

| 3,299,038 A * | 1/1967 | Tomcufcik et al. ........... 534/553 |
| 3,907,767 A | 9/1975 | Hess et al. |
| 3,932,633 A | 1/1976 | O'Brien et al. |
| 3,976,633 A | 8/1976 | Berkoff et al. |
| 4,923,970 A | 5/1990 | Michejda et al. |
| 2002/0155172 A1 * | 10/2002 | Yuan et al. .................... 424/692 |

FOREIGN PATENT DOCUMENTS
GB            893437        4/1962

OTHER PUBLICATIONS

Virag, Andrej et al.., "Synthesis and Characterization of New Triazenide Salts", Journal of Organic Chemistry, 71, 4014-4017, 2006.*
Golub et al., Science, 286, 531-537, 1999.*
Stefane, Bogdan et al, "3-Acyl-1,3-Diaryltriazees as Neutral and Selective Acylating Agents", Tetrahedron Letters, 42, 6659-6662, 2001.*
Pilch, et al.; "Berenil [1,3-Bis(4'-Amidinophenyl)Triazene] Binding to DNA Duplexes and to RNA Duplex—Evidence for Both Intercalative and Minor Groove Binding Properties"; Biochem 34; (1995); pp. 9962-9976.
Mickisch, et al.; Urol Res 18 (1990); pp. 131-136; "Chemosensitivity testing of primary human renal cell carcinoma by a tetrazolium based microculture assay (MTT)".
Brown, et al.; Crystal Structure of a Berenil—Dodecanucleotide Complex: The Role of Water in Sequence-Specific Ligand Binding; EMBO J 9; (1990); pp. 1329-1334.
Serrone et al.; "Dacarbazine-Based Chemotherapy for Metastatic Melanoma: Thirty-Year Experience Overview" J Exp Clin Cancer Res 19 (2000) 21; pp. 21-34.
Olliaro, et al.; "Developments in the Treatment of Leishmaniasis and Trypanosomiasis" Expert Opin Emerg Drugs 7; (2002); pp. 61-67.
Beketić-Orešković et al., Neoplasma 41 (1994) pp. 171-176 "Human larynx carcinoma cells resistant to cis-diamminedichloroplatinum(II): cross-resistance patterns".
International Search Report; PCT/HR2010/000006; Jun. 8, 2010; 2 pages.
Advani et al.; "Management of Advanced Stage Hodgkin Lymphoma"; J Natl Comp Canc Netw 4 241; Mar. 2006; pp. 241-247.
Brandsma, et al.; "Molecular Targeted Therapies and Chemotherapy in Malignant Gliomas"; Curr Opin Oncol 19 (2007); pp. 598-605.
McConnaughie and Jenkins; "Novel Acridine—Triazenes as Prototype Combilexins: Synthesis, DNA Binding, and Biological Activity"; J Med Chem 38; (1995); pp. 3488-3501.
Nifontov Vi et al: "Reactivity and mechanism of acti on of triazenes XIII. Correlation of structure, reactivity and biological activity of 3,3-dimethyltriazenes and other cryptodiazonium transport forms of cytotoxic diazo derivatives" Pharmaceutical Chemistry Journal, vol. 28, No. 9, 1994, pp. 611-615.
Osmak et al., Mutat Res 303 (1993) pp. 113-120; "Resistance of human larynx carcinoma cells to cisplatin, gamma-irradiation and methotrexate does not involve overexpression of c-myc or c-Ki-ras oncogenes".
Quirt, et al.; "Temozolomide for the treatment of metastatic melanoma"; Curr Oncol 14 (2007); pp. 27-33.
S.S. Agarwala; J.M. Kirkwood; "Temozolomide, a novel alkylating agent with activity in the central nervous system, may improve the treatment of advanced metastatic melanoma"; Review. Oncologist 5; (2000); pp. 144-151.
Osmak and Eljuga, Res Exp Med 193; (1993); pp. 389-396; "The characterization of two human cervical carcinoma HeLa sublines resistant to cisplatin".
Marchesi, et al.; "Triazene Compounds: Mechanism of Action and Related DNA Repair Systems"; Pharmacol Res 56 (2007); pp. 275-287.

* cited by examiner

*Primary Examiner* — Fiona T Powers
(74) *Attorney, Agent, or Firm* — St. Onge Steward Johnston & Reens LLC

(57) ABSTRACT

The present invention refers to analogues of 1,3-bis(4-nitrophenyl)triazenes, their pharmaceutically acceptable salts and N-acyl derivatives for the treatment of different types of tumors. Said compounds show cytotoxicity at very low concentrations ($IC_{50}$ 0.22 to 12.8 μM), and good solubility. These compounds can be used in the treatment of tumor patients as single drugs or in combination with other cytostatics.

13 Claims, No Drawings

ANALOGUES OF 1,3-BIS(4-NITROPHENYL)TRIAZENES, THEIR PHARMACEUTICALLY ACCEPTABLE SALTS AND N-ACYL DERIVATIVES FOR TUMOUR TREATMENT

CROSS-REFERENCE TO RELATED APPLICATIONS

The present application is a continuation of pending International Patent Application PCT/HR2010/000006 filed on Mar. 9, 2010 which designates the United States and claims priority from Croatian Patent Application P20090144A filed on Mar. 11, 2009, the content of which is incorporated herein by reference.

FIELD OF THE INVENTION

The present invention relates to triazene compounds and thei use in the treatment of cancers and other tumours.

BACKGROUND OF THE INVENTION

Nowadays, humans are increasingly exposed to different types of stress. In addition, human population is getting older every day. Those are only few of the factors involved in the increased number of tumour patients all over the world. Due to the increased number of tumour patients, as well as due to the relatively low efficacy of the current tumour treatments, there is a growing need for a more efficient tumour treatment, i.e., more efficient anti-tumour agent to be used in said treatments. Most tumours belong to the group of the so called solid tumours, such as breast tumour, ovary tumour, prostate gland tumour, lung tumour etc., while leukemia and lymphomas belong to the group of hematological tumours. Successful treatment of tumour patients has not yet been achieved— every third patient dies of said disease. Therefore, enormous efforts have been invested in the development of new, more successful types of tumour treatment.

Chemotherapy is the method of choice in tumour treatment. In classical chemotherapy, which is still the most used treatment, drugs with a stronger effect on dividing cells (where cell division is one of the main characteristics of tumour cells) are used. The particular problem of this type of treatment is the development of tumour cell resistance. Thereupon, tumour cells use maximally all molecular protective mechanisms (that are active in normal cells) to protect themselves from the treatment. Due to selective pressure caused by chemotherapy, the number of resistant tumour cells increases, which finally leads to insufficient efficiency of classical cytostatics in tumour treatment. Thus, insufficient efficiency of the existing tumour treatments raises the need for new, more effective compounds, as well as for the new strategies of tumour treatment.

Publications disclosing the efficiency of compounds having triazene group are being published from 1980 until present. They are mainly related to the group of alkylating agents having similar chemical, physical, anti-tumour and mutagenic characteristics: dacarbazine, procarbazine, mitozolomide, and the newest temozolomide. Some of the above said alkylating agents are already used in clinical practise (Serrone et al., *J Exp Clin Cancer Res* 19(2000)21; Advani et al., *J Natl Comp Canc Netw* 4(2006)241; Cassier et al., *Expert Opin Emerg Drugs* 12(2007)139; Brandsma et al., *Curr Opin Oncol* 19(2007)598; Quirbt et al., *Curr Oncol* 14(2007)27). Mechanism of their action is mainly based on methylation of the $0^6$ position of guanine in the DNA. These adducts cause mismatched bases that can finally lead to cell death or, if cells survive, to somatic mutations. Unfortunately, during the tumour therapy, cell resistance to said compounds, based on increased level/activity of enzyme $O^6$-alkylguanine-DNA-alkyl transferase, is developed (Marchesi i sur., *Pharmacol Res* 56(2007)275).

Another known compound having three nitrogen atoms in its structure is Berenil (Brown et al., *EMBO J* 9(1990)1329). This triazene has two protonated amidine $NH_2$ groups (electron acceptors, which as a part of the larger $C(NH_2)_2^+$ group act as electron-withdrawing groups). Berenil binds into the minor groove of DNA molecules (Pilch et al., *Biochem* 34(1995)9962) thus inhibiting the processes linked to DNA: from cell division to gene transcription. The published results showed its toxicity to tropical parasites from the genera *Trypanosoma* and *Leischmania* (Olliaro et al., *Expert Opin Emerg Drugs* 7(2002)61). There is only one publication in which the cytotoxicity of berenil was examined on mammalian cells. Said compound showed very low activity ($IC_{50}$>100 µM). However, by binding to chromophore acridine, which intercalates in DNA, its activity was significantly increased (Mc Connaughie and Jenkins, *J Med Chem* 38(1995)3488).

Patent GB 893 437 describes therapeutic compositions comprising substituted triazenes, which are used for tumour treatment. Therefore, the compounds used in accordance with this patent have triazene-based structure. Said compounds show selective activity for adenocarcinoma in mammals (72j). Some of described compounds also contain two phenyl groups having different substituent. However, none of the mentioned compounds have nitro substituent on both phenyl groups.

U.S. Pat. No. 4,923,970 describes the new substituted 1-(2-chloroethyl)-3-acyl-3-alkyl-triazenes and the method of their synthesis. Said compounds bind to DNA and induce its cross-linking causing cell death. The compounds of the above mentioned patent are not bis-substituted triazenes and have chloroethyl group on nitrogen atom of triazene. Considering that all compounds disclosed with the present invention are bis-substituted compounds, and none of them has the chloroethyl group on the nitrogen atom, the compounds of the present invention differ from the compounds as described in the above mentioned patent.

U.S. Pat. No. 3,976,633 describes bis-substituted cyanotrifluoromethylphenyl triazenes which help the regulation of body weight. Even though the compounds of this patent have triazene-based structure, their substituent groups differ from the substituent groups of the present invention, meaning that the compounds are, thus, not similar. In addition, this patent refers to compounds effective in the regulation of body weight, which is not the subject-matter of the present invention.

U.S. Pat. No. 3,299,038 describes carboxamide 3-triazenes showing anti-inflammatory effect and the method of their synthesis. One of the starting compounds used for the synthesis of such compounds is 1,3-bis-(4-nitrophenyl)triazene. Given that this compound is only the starting substance for the synthesis of the compounds protected by this patent, its role in the present invention is only of chemical nature.

U.S. Pat. No. 3,932,633 describes o-triazenobenzamides and their application in the prevention and treatment of aggressive behaviour of patients. The compounds have benzamide group that does not appear as substituent in the present invention. Therefore, these compounds differ from the compounds disclosed in the present invention.

U.S. Pat. No. 3,907,767 describes 1-phenyl-3-hydroxy-3-methyltriazenes and the method of their synthesis. The compounds contain only one phenyl group, differing, thus, from the compounds referred to in the present invention.

The treatment of tumours is usually based on combination of different medical interventions such as surgical elimination of the tumour, chemotherapy or radiation. In chemotherapy chemical substances of natural or synthetic origin are used for systemic tumour treatment and tumour cell division is controlled chemically. Most cytostatics used in classical chemotherapy damage DNA by disturbing its synthesis and/or function, having death of tumour cells as a result.

One of the limiting factors in the tumour treatment with cytostatics is the development of tumour cell resistance. Drug resistance is mostly caused by genetic instability of tumour cells and their increased capacity to adapt to unfavourable growth conditions, such as therapy, and to activate different molecular mechanisms to develop resistance. Acquired drug resistance during chemotherapy is well known for standard cytostatics such as cisplatin, doxorubicin etc. In addition to developed resistance to the cytostatic used for treating the tumour, a cross-resistance to other cytostatics, which are completely different by structure and activity, is usually developed. Therefore, tumour cells resistant to cisplatin may become cross-resistant to carboplatin, doxorubicin, melphalan, methotrexate etc. To which additional compounds cross-resistance will be developed depends on the cytostatic itself, its administration route, as well as on the tumour cell type and status.

In order to inhibit the development of tumour cell resistance to cytostatics, a combination of several (usually 2-3) cytostatics, which kill tumour cells by different mechanisms, is used nowadays.

Due to development of cross-resistance to classical cytostatics, new compounds that target tumour cells through different mechanisms would be most welcome. The use of combination of classical cytostatics with new compounds in tumour therapy would reduce cross-resistance development.

SUMMARY OF THE INVENTION

It is an object of the invention to provide compounds that can be used in tumour treatment. Primarily, these compounds are highly cytotoxic. The cytotoxicity threshold for the potential anti-tumour compounds is $IC_{50}$ lower than 100 µM. The lower the $IC_{50}$ value the higher cytotoxic potential.

It is an object of the invention to provide compounds with good solubility properties, which can reach the tumour cells and destroy them.

It is a further object of the invention to provide compounds that can be used in tumour treatment in combination with standard cytostatics in order to inhibit the development of tumour cell resistance to drug treatment.

The present invention comprises analogues of 1,3-bis(4-nitrophenyl)triazenes, their pharmaceutically acceptable salts and N-acyl derivatives, and methods of use thereof to that inhibit cell division and for the treatment of cancers and other types of tumours. These highly cytotoxic compounds have in their structure two $NO_2$ groups which, due to their properties, belong to electron-withdrawing groups. The synthesis of pharmaceutically acceptable triazene salts increases the solubility of triazenes.

Thus, the present invention provides the analogues of 1,3-bis(4-nitrophenyl)triazenes for the treatment of tumour diseases in human patients, where the analogues are represented by general formula I:

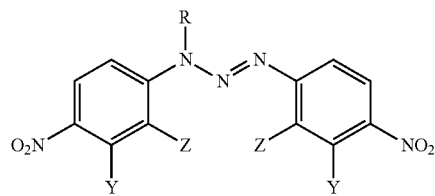

where
R is H
Z is X, $CX_3$, alkyl ester ($C_1$-$C_{10}$), CN, alkyl ($C_1$-$C_{10}$);
Y is H, X, $CX_3$, alkyl ester ($C_1$-$C_{10}$), CN, alkyl ($C_1$-$C_{10}$)
X is halogen.

Also, the present invention provides the pharmaceutically acceptable salts of 1,3-bis(4-nitrophenyl)triazenes for the treatment of tumour diseases in human patients where the pharmaceutically acceptable salts are represented by general formula II:

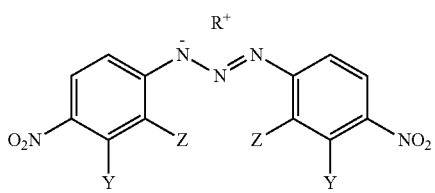

where
$R^+$ is $Et_3NH^+$, $K^+$, $(HOCH_2CH_2)_3NH^+$, $H_2N^+$=$C(NH_2)NH(CH_2)_3CH(NH_2)COOH$
Z is X, $CX_3$, alkyl ester ($C_1$-$C_{10}$), CN, alkyl ($C_1$-$C_{10}$);
Y is H, X, $CX_3$, alkyl ester ($C_1$-$C_{10}$), CN, alkyl ($C_1$-$C_{10}$)
X is halogen.

It is preferable that in the pharmaceutically acceptable salts of general formula II, $R^+$ is $H_2N^+$=$C(NH_2)NH(CH_2)_3CH(NH_2)COOH$.

It is preferable that in the above mentioned compound of formula II, Y is hydrogen, Z is Br and $R^+$ is $H_2N^+$=$C(NH_2)NH(CH_2)_3CH(NH_2)COOH$.

The present invention also provides N-acyl compounds of 1,3-bis(4-nitrophenyl)triazenes for the treatment of tumour diseases in human patients, represented by general formula III:

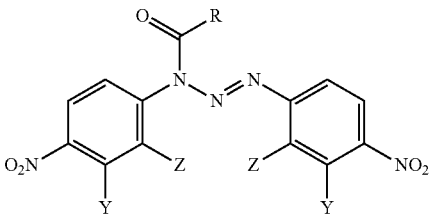

where
R is halomethyl, alkyl ($C_1$-$C_{10}$), alkoxy ($C_1$-$C_{10}$), benzyl, phenyl, halophenyl, alkylphenyl ($C_1$-$C_{10}$), 1-naphthyl, halo-1-naphthyl, alkyl-1-naphthyl ($C_1$-$C_{10}$), 2-naphthyl, halo-2-naphthyl, alkyl-2-naphthyl ($C_1$-$C_{10}$), 2-(trihalomethyl)phenyl, 3-(trihalomethyl)phenyl, 4-(trihalomethyl)phenyl, 2-halophenyl, 3-halophenyl, 4-halophenyl, pentafluorophenyl;
Z is X, $CX_3$, alkyl ester ($C_1$-$C_{10}$), CN, alkyl ($C_1$-$C_{10}$);
Y is H, X, $CX_3$, alkyl ester ($C_1$-$C_{10}$), CN, alkyl ($C_1$-$C_{10}$)
X is halogen.

Further, it is preferable that in the abovementioned compound of general formula III, Y is hydrogen, Z is Cl and R is chloromethyl.

It is preferable that in the abovementioned compound of general formula III, Y is hydrogen, Z is Cl and R is benzyl.

It is preferable that in the abovementioned compound of general formula III, Y is hydrogen, Z is Cl and R is phenyl.

It is preferable that in the abovementioned compound of general formula III, Y is hydrogen, Z is Cl and R is methoxy group.

In the present invention the terms "halogen" and "halo" refer to halogen elements selected from: F, Cl, Br and I.

The compounds of the present invention have demonstrated good solubility. Their solubility was particularly good in dimethyl sulfoxide. In spite of the good solubility of the compounds of subject invention in dimethyl sulfoxide, that does not limit their solubility in other solvents that are not stated in the present invention.

Testing of the compounds of the present invention showed high sensitivity of parental tumour cells to said compounds, as well as of their sub-lines which both are resistant to standard cytostatics. It also showed lower sensitivity of normal cells to said compounds. The cytotoxicity of the compounds of the present invention to tumour cells will be more described in the detailed description of the present invention. During the testing of the compounds of the present invention, the compound 1,3-bis(4-nitrophenyl)triazene was tested as well, but it did not show any biological activity.

The compounds of the present invention can be used as single-drug therapy for tumour in humans. Besides, since testings have shown that the compounds of the present invention do not bind to DNA, i.e. do not affect DNA, they could be used in combination with the cytostatics which affect DNA (such as cisplatin), due to their different mechanism of action.

Therefore, the compounds of the present invention can be used as the active substances in different pharmaceutical compositions for the treatment of tumour in humans.

DETAILED DESCRIPTION OF THE INVENTION

Some of the typical examples of synthesis of the compounds of the present invention will be described hereinafter. The names of the compounds used in the present invention correspond to the test names of the compounds as shown in Table 1, where substituent used in particular compounds is shown.

Example 1

Synthesis of the Compound VM-94c

L-arginine (0.1 mmol, 17.5 mg) was added to the solution of 1,3-bis(2-bromo-4-nitrophenyl)triazene (0.1 mmol; 44.5 mg) in acetone (2 mL) and $CH_2Cl_2$ (1 mL). The colour of the solution changed immediately from yellow to dark red. The reaction mixture was stirred for 2 h at room temperature, the solid material was filtered and washed with $CH_2Cl_2$ (1 mL) to obtain the compound VM-94c (23.6 mg; 38% yield).

Example 2

Synthesis of N-acyl-1,3-bis(4-nitrophenyl)triazenes; Specifically, Synthesis of the Compound BA-196

Triethylamine (1.1 mmol; 111 mg) was added at room temperature to the solution of 1,3-bis(2-chloro-4-nitrophenyl)triazene (0.50 mmol; 178 mg) in acetonitrile (5 mL). Thereafter, 3-(trifluoromethyl)benzoyl chloride (1.0 mmol; 215 mg) was added and the reaction mixture was stirred for 30 min at room temperature in order to evaporate the liquid under reduced pressure. The residue was treated with $CH_2Cl_2$ (15 mL) and water (4 mL). Subsequently, two phases were separated and the water phase was extracted with $CH_2Cl_2$ (3×5 mL). Combined dichloromethane extracts were dried over anhydrous sodiumسulfate, filtered and evaporated. The oily residue was dissolved in hot ethyl acetate (1 mL) and petroleum ether was added-drop wise (10 mL). The solid material was filtered off to obtain the compound BA-196 (183 mg; 69% yield).

Biological Tests

The human cervical carcinoma HeLa cells were used as a model for testing the cytotoxicity of new compounds. Said cells grow as single-layer culture in nutrient Dulbecco's modified Eagle's medium (DMEM, Gibco Life Technologies, Grand Island, USA) with 10% of fetal bovine serum (Gibco) and antibiotics (penicillin 100 U, streptomicine 0.1 mg, Sigma Chem. Co., St. Louis, USA). They were grown in thermostat at 37° C. with 5% $CO_2$ in a humidified atmosphere in plastic cell culture flasks (BD Falcon, Germany). The cytotoxicity of the compound VM-94c was tested also on tumour cells of different origin: glioblastoma A1235 cells, laryngeal carcinoma HEp-2 cells, rhabdomiosarcoma RD cells, ovarian adenocarcinoma OVCAR cells, human embryonic kidney HEK 293 cells with unlimited cell division capacity and normal human cells that were grown as described above.

The compounds were dissolved in dimethyl sulfoxide (Merck, Darmstadt, Germany) in concentrations of 20-120 mM (depending on the compound) and stored in aliquots at −20° C. as stock solutions. The stock solutions were diluted to the appropriate concentrations just before the experiments.

The cytotoxicity of new compounds was determined by spectrophotometric MTT method (Michisch et al., *Urol Res* 18(990)131). It is a colorimetric method based on the ability of living cells to reduce the yellow tetrazolium salt 3-(4,5-dimethylthiazol-2-yl)-2,5-diphenyltetrazolium bromide) (MTT; Merck) to violet formazane crystals using mitochondrial dehydrogenase and cytochrome b and c. The crystals were dissolved in dimethyl sulfoxide (DMSO), followed by spectrophotometric measurement of their absorbance at 545 nm.

Cells were seeded in 96-well microtitration plates (BD Falcon) (2.5×10$^3$/180 µl), and incubated overnight at temperature of 37° C. to allow the cells to attach to the growth medium. Next day the compounds were added to the growth medium in a wide range of concentrations, from 0.05 to 100 µM (each concentration in quadruplicate). After 72 hours, the samples were coloured with the MTT dye and left for 3 hours in the thermostat. Formed crystals were dissolved in dimethyl sulfoxide and the absorbance of each sample was measured at 545 nm. The survival of cells was calculated according to the formula:

$$\% \text{ survival} = \frac{\text{absorbance of treated cells} - \text{absorbance of blind } probe^*}{\text{absorbance of untreated cells} - \text{absorbance of blind } probe^*} \times 100$$

*blind probe = growth medium without cells with the compound and MTT dye.

The experiments were repeated 2-3 times. On the basis of these results cell survival curve was made and cell survival mean values and standard deviations were calculated. $IC_{50}$ values were read from the curve. $IC_{50}$ is the concentration of a compound that reduces the survival of treated cells to 50%.

In Table 1 $IC_{50}$ values of the compounds of the present invention are represented. Said compounds show significant cytotoxicity even at very low concentrations. The cytotoxicity threshold for the biologically active compounds is 100 µM. For the compounds of the present invention $IC_{50}$ ranges from 0.22 to 12.8 µM.

TABLE 1

The structure and the cytotoxicity of some of the compounds of the present invention:

| Compounds | Substituents | Test name of compound | Cytotoxicity ($IC_{50}\,\mu M$) |
|---|---|---|---|
| Compound of formula III | Z = Cl; Y = H; R = chloromethyl | KLN-2 | 0.58 |
| Compound of formula III | Z = Cl; Y = H; R = benzyl | KLN-3 | 0.57 |
| Compound of formula III | Z = Cl; Y = H; R = phenyl | KLN-4 | 0.61 |
| Compound of formula III | Z = Cl; Y = H; R = methoxy | KLN-5 | 0.88 |
| Compound of formula III | Z = $CF_3$; Y = H; R = chloromethyl | BA-170 | 0.6 |
| Compound of formula III | Z = $CF_3$; Y = H; R = phenyl | BA-171 | 0.45 |
| Compound of formula III | Z = $CF_3$; Y = H; R = 4-(trifluoromethyll)phenyl | BA-172 | 0.59 |
| Compound of formula III | Z = $CF_3$; Y = H; R = pentafluorophenyl | BA-174 | 1.1 |
| Compound of formula III | Z = Br; Y = H; R = phenyl | BA-177 | 1.6 |
| Compound of formula III | Z = Cl; Y = H; R = 4-(trifluoromethyl)phenyl | BA-178 | 1.9 |
| Compound of formula III | Z = $CF_3$; Y = H; R = 3-(trifluoromethyl)phenyl | BA-189 | 0.6 |
| Compound of formula III | Z = $CF_3$; Y = H; R = 3-fluorophenyl | BA-190 | 0.83 |
| Compound of formula III | Z = $CF_3$; Y = H; R = 2-fluorophenyl | BA-193 | 0.8 |
| Compound of formula III | Z = Br; Y = H; R = 3-(trifluoromethyl)phenyl | BA-195 | 1.1 |
| Compound of formula III | Z = Cl; Y = H; R = 3-(trifluoromethyl)phenyl | BA-196 | 1.35 |
| Compound of formula III | Z = Br; Y = H; R = 2-fluorophenyl | BA-197 | 0.9 |
| Compound of formula III | Z = Cl; Y = H; R = 2-fluorophenyl | BA-198 | 2.4 |
| Compound of formula III | Z = Cl; Y = H; R = 3-fluorophenyl | BA-201 | 2.5 |
| Compound of formula III | Z = Br; Y = H; R = 4-fluorophenyl | BA-202 | 0.55 |
| Compound of formula III | Z = $CF_3$; Y = H; R = 2-(trifluoromethyl)phenyl | BA-206 | 5.0 |
| Compound of formula III | Z = Br; Y = H; R = 2-(trifluoromethyl)phenyl | BA-207 | 12.8 |
| Compound of formula III | Z = Cl; Y = H; R = 2-(trifluoromethyl)phenyl | BA-208 | 11.1 |
| Compound of formula II | Z = $CF_3$; Y = H; $R^+$ = $Et_3NH^+$ | VM-81 | 0.22 |
| Compound of formula II | Z = Br; Y = H; $R^+$ = $Et_3NH^+$ | VM-83 | 0.45 |
| Compound of formula II | Z = Br; Y = H; $R^+$ = $H_2N^+$ = $C(NH_2)NH(CH_2)_3CH(NH_2)COOH$ | VM 94c | 3.65 |
| Compound of formula II | Z = Br; Y = H; $R^+$ = $K^+$ | VM-97 | 0.45 |
| Compound of formula II | Z = Cl; Y = H; $R^+$ = $(HOCH_2CH_2)_3NH^+$ | VM-102 | 2.6 |

The cytotoxicity of the new compounds was determined on human cervical carcinoma HeLa cells by the spectrophotometric MTT method. It is expressed as $IC_{50}$ value, i.e. as the concentration of a compound that reduces cell survival to 50%.

The analysis of the cytotoxicity related to the structure of the compound shows that biologically active compound has two electron-withdrawing groups ($NO_2$) at each benzene ring. The other group that significantly increases the cytotoxicity of 1,3-bis(4-nitrophenyll)triazenes is to be bound at both orto positions with respect to the triazene moiety. Introduction of orto substituents comprising halogen clearly influences cytotoxic activity of the said compounds in the following order: $CF_3$>Br>Cl>F (Table 1).

In particular, it should be pointed out that the pharmaceutically acceptable triazene salt with arginine (as in compound VM-94c) has significantly increased the compound's solubility, making it more suitable for possible clinical application (similar positive effect of arginine, namely increased solubility, can be expected also for other salts of general formula II where R is arginine).

The cytotoxicity of compound VM-94c was tested on several tumour cell lines of different origin. Said triazene resulted cytotoxic for all examined tumour cell lines even at very low concentrations. The cytotoxicity was dependent on the cell type: human ovarian adenocarcinoma OVCAR cells were the most sensitive, while laryngeal carcinoma (HEp-2) cells were less sensitive. The least sensitive were embryonic kidney HEK 293 cells with unlimited cell division capacity, as well as the normal human cells, keratinocytes (Table 2).

TABLE 2

Cytotoxicity of the compound VM-94c against different tumour and normal cell lines

| | Cell | | | | | |
|---|---|---|---|---|---|---|
| HeLa | A1235 | HEp-2 | RD | OVCAR | HEK 293 | Keratinocytes |
| $IC_{50}$, $\mu M$ 3.65 | 5.45 | 5.5 | 5.1 | 3.4 | 7.9 | 9.45* |

Cytotoxicity of the triazene VM-94c was determined on tumour cells of different origin: HeLa=cervical carcinoma cells, A1235=glioblastoma cells, HEp2=laryngeal carcinoma cells, RD=rhabdomyosarkoma cells, OVCAR=ovarian adenocarcinoma cells, HEK 293=embryonic kidney cells with unlimited division, keratinocytes=normal human cells. The cytotoxicity was determined by spectrophotometric MTT method (except for keratinocytes, which have low metabolic activity, so their survival was determined by addition of crystal violet dye) and expressed as $IC_{50}$.

Nowadays the market offers a series of the so called smart drugs targeting tumour specific molecules. Nevertheless, the majority of tumour patients are still treated with classical chemotherapy. Since the major impediment for the success of such chemotherapy is the development of tumour cell resistance, a combination of 2-3 cytostatics with different mechanisms of action is usually used in order to increase their efficiency and reduce the possibility of tumour cell resistance development. The subject compounds of the present invention can be used in such combination, considering that equal sensitivity to compound VM-94c in cervical carcinoma and laryngeal carcinoma cells and their sub-lines resistant to standard anti-tumour drugs was observed (Table 3).

TABLE 3

Cytotoxicity of compound VM-94c against two pairs of tumour parental cells and their sub-lines resistant to standard cytostatics

| | Cells | | | |
|---|---|---|---|---|
| | HeLa | HeLa CK | HEp2 | CA3 |
| $IC_{50}$ (μM) | 3.4 | 3.9 | 5.5 | 7.2 |

Cytotoxicity of VM-94c triazene was tested on two pairs of parental tumour cells and their sub-lines resistant to standard cytostatics. It was tested on parental cervical carcinoma HeLa cells and their sub-line HeLa CK cells resistant to cisplatin and cross-resistant to vincristine and methotrexate (Osmak and Eljuga, *Res Exp Med* 193(1993) 389). It was also tested on laryngeal carcinoma HEp-2 cells and their sub-line CA3 cells resistant to cisplatin and cross-resistant to vincristine, methotrexate and mitomycin C (Osmak et al., *Mutat Res* 303 (1993) 113; Beketić-Orešković et al., *Neoplasma* 41 (1994) 171). Cytotoxicity was determined by spectrophotometric MTT method and expressed as $IC_{50}$.

During the testing of the compounds of present invention their activity towards DNA, i.e. their binding to DNA, on the basis of two methods was examined as well. In the first method double stranded DNA was mixed with selected compound and thereafter the DNA melting point was determined. If a compound binds to DNA, the melting point of DNA will change. That was not the case for the compounds of the present invention. In the second method UV spectra of a compound were recorded before and after mixing with DNA. This method examines the binding of the compounds having benzene rings in the structure to DNA, as in the compounds of the present invention. If a compound binds to DNA, its UV spectrum will change. The UV spectra of the compounds from the present invention did not change. Therefore, the compounds from the present invention do not bind to DNA and do not affect DNA during tumour treatment.

What is claimed is:

1. An analogue of 1,3-bis(4-nitrophenyl)triazene, represented by formula I:

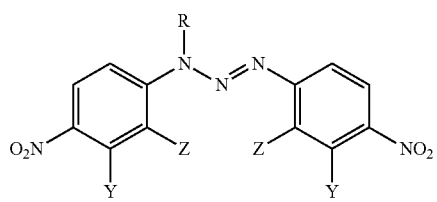

wherein
R is H
Z is $CX_3$,
Y is H; and
X is halogen.

2. A pharmaceutically acceptable salt of the analogue of 1,3-bis(4-nitrophenyl)triazene represented by formula II:

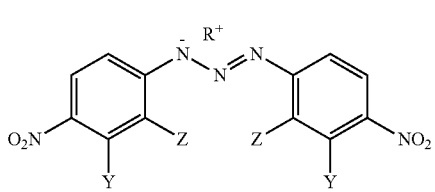

wherein
$R^+$ is $K^+$, $(HOCH_2CH_2)_3NH^+$ or $H_2N^+$=$C(NH_2)NH(CH_2)_3CH(NH_2)COOH$;
Z is X or $CX_3$,
Y is H; and
X is halogen.

3. The pharmaceutically acceptable salt of claim 2, wherein $R^+$ is $H_2N^+$=$C(NH_2)NH(CH_2)_3CH(NH_2)COOH$.

4. The pharmaceutically acceptable salt of claim 2 wherein Z is Br, and $R^+$ is $H_2N$+=$C(NH_2)NH(CH_2)_3CH(NH_2)COOH$.

5. An N-acylated compound of 1,3-bis(4-nitrophenyl)triazene represented by formula III:

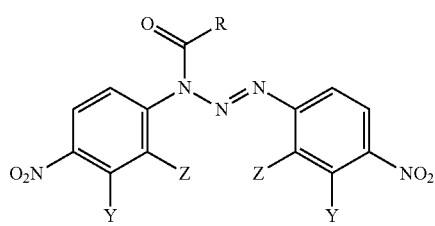

wherein
R is halomethyl, alkoxy ($C_1$-$C_{10}$), phenyl, halophenyl, 2-(trihalomethyl)phenyl, 3-(trihalomethyl)phenyl, 4-(trihalomethyl)phenyl, 2-halophenyl, 3-halophenyl, 4-halophenyl; or pentafluorophenyl;
Z is X or $CX_3$, wherein
Y is H; and
X is halogen with the provisio that Z is not X when R is alkoxy ($C_1$-$C_{10}$).

6. The N-acylated compound of 1,3-bis(4-nitrophenyl)triazene of claim 5, wherein Z is Cl, and R is chloromethyl.

7. The N-acylated compound of 1,3-bis(4-nitrophenyl)triazene of claim 5, wherein Z is Cl, and R is phenyl.

8. A pharmaceutical formulation comprising at least one of the following compounds:
(a) an analogue of 1,3-bis(4-nitrophenyl)triazene, represented by general formula I:

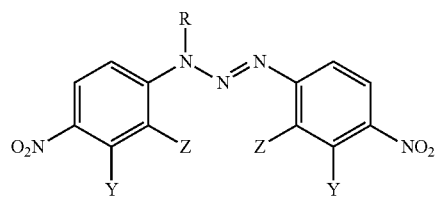

wherein
R is H
Z is CX$_3$,
Y is H; and
X is halogen; or
(b) a pharmaceutically acceptable salt of the analogue of 1,3-bis(4-nitrophenyl)triazene represented by formula II:

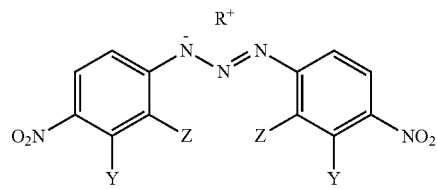

wherein
R$^+$ is K$^+$, (HOCH$_2$CH$_2$)$_3$NH$^+$ or H$_2$N$^+$=C(NH$_2$)NH(CH$_2$)$_3$CH(NH$_2$)COOH
Z is X or CX$_3$;
Y is H; and
X is halogen; or
(c) an N-acylated compound of 1,3-bis(4-nitrophenyl)triazene represented by formula III:

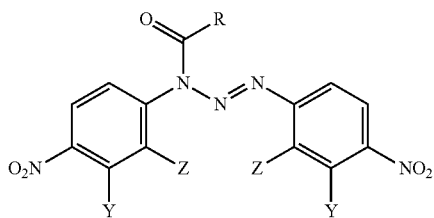

wherein
R is halomethyl, alkoxy (C$_1$-C$_{10}$), phenyl, halophenyl, 2-(trihalomethyl)phenyl, 3-(trihalomethyl)phenyl, 4-(trihalomethyl)phenyl, 2-halophenyl, 3-halophenyl, 4-halophenyl or pentafluorophenyl;
Z is X or CX$_3$; wherein
Y is H; and
X is halogen.

9. The pharmaceutical formulation of claim 8, wherein the compound is the pharmaceutically acceptable salt of the analogue of 1,3-bis(4-nitrophenyl)triazene represented by the formula II and wherein R$^+$ is H$_2$N$^+$=C(NH$_2$)NH(CH$_2$)$_3$CH(NH$_2$)COOH.

10. The pharmaceutical formulation of claim 8, wherein the compound is the pharmaceutically acceptable salt of the analogue of 1,3-bis(4-nitrophenyl)triazene represented by the formula II and wherein Z is Br, and R$^+$ is H$_2$N$^+$=C(NH$_2$)NH(CH$_2$)$_3$CH(NH$_2$)COOH.

11. The pharmaceutical formulation of claim 8, wherein the compound is the N-acylated compound of 1,3-bis(4-nitrophenyl)triazene represented by the formula III, and wherein Z is Cl, and R is chloromethyl.

12. The pharmaceutical formulation of claim 8, wherein the compound is the N-acylated compound of 1,3-bis(4-nitrophenyl)triazene represented by the formula III, and wherein Z is Cl, and R is phenyl.

13. The pharmaceutical formulation of claim 8, wherein the compound is the N-acylated compound of 1,3-bis(4-nitrophenyl)triazene represented by the formula III, and wherein Z is Cl, and R is methoxy.

* * * * *